United States Patent [19]

Kadkade

[11] 4,038,778
[45] Aug. 2, 1977

[54] TISSUE CULTURE TECHNIQUE FOR ASEXUAL PLANT REPRODUCTION AND A MEDIUM FOR USE THEREWITH

[75] Inventor: Prakash G. Kadkade, Marlboro, Mass.

[73] Assignee: GTE Laboratories Incorporated, Waltham, Mass.

[21] Appl. No.: 727,323

[22] Filed: Sept. 27, 1976

[51] Int. Cl.$^2$ ............................................. A01G 31/00
[52] U.S. Cl. ............................................................ 47/58
[58] Field of Search .................................................. 47/58

[56] References Cited

U.S. PATENT DOCUMENTS

| | | | |
|---|---|---|---|
| 2,747,334 | 5/1956 | Routien et al. | 47/58 |
| 3,514,900 | 6/1970 | McDade | 47/58 |
| 3,683,550 | 8/1972 | Corlett et al. | 47/58 |
| 3,816,960 | 6/1974 | Gudin et al. | 47/58 |
| 4,003,156 | 1/1977 | Sibi et al. | 47/58 |

FOREIGN PATENT DOCUMENTS

| | | | |
|---|---|---|---|
| 1,387,821 | 3/1975 | United Kingdom | 47/58 |

OTHER PUBLICATIONS

The Control of Growth in Plant Cells, Steward, Scientific Amer., Oct. 1963, pp. 104-113.
Propagation of Asparagus —, Hasegawa et al., J. Amer. Soc. Hort. Sci., 98(2), pp. 143-148, 1973.
Propagation of —, Meyer et al., Hortscience, Oct. 1975, pp. 479-480.

Primary Examiner—Robert E. Bagwill
Attorney, Agent, or Firm—Irving M. Kriegsman; Robert A. Seldon

[57] ABSTRACT

A tissue culture technique and a culture medium used therewith for asexually propagating a plurality of plants of the family Cruciferae are disclosed.

According to one aspect of the invention, an excised portion of a donor plant is placed in a culture medium comprising organic and inorganic salts and a preferable concentration of 1 mg/l of Indoleacetic Acid, 0.5 mg/l of Kinetin and 40 mg/l of Adenine Sulfate. The medium induces the simultaneous initiation of buds and roots by the explant to form a plurality of plantlets which may be transplanted into soil for the timely initiation of food and medicinal crops.

In accordance with a second aspect of the invention, the pre-culture storage of the requisite plant part in a convenient, disease-free, and pest-free manner is disclosed whereby callus from the excised portion of the donor plant is maintained on a first medium for subsequent transfer to the medium described above. The callus is initiated and maintained, for periods in the order of a year or more, on a medium containing organic and inorganic salts and preferable concentrations of 1.86 mg/l of naphthaleneacetic acid and 2.25 mg/l of $N_6$-Benzyladenine.

11 Claims, 1 Drawing Figure

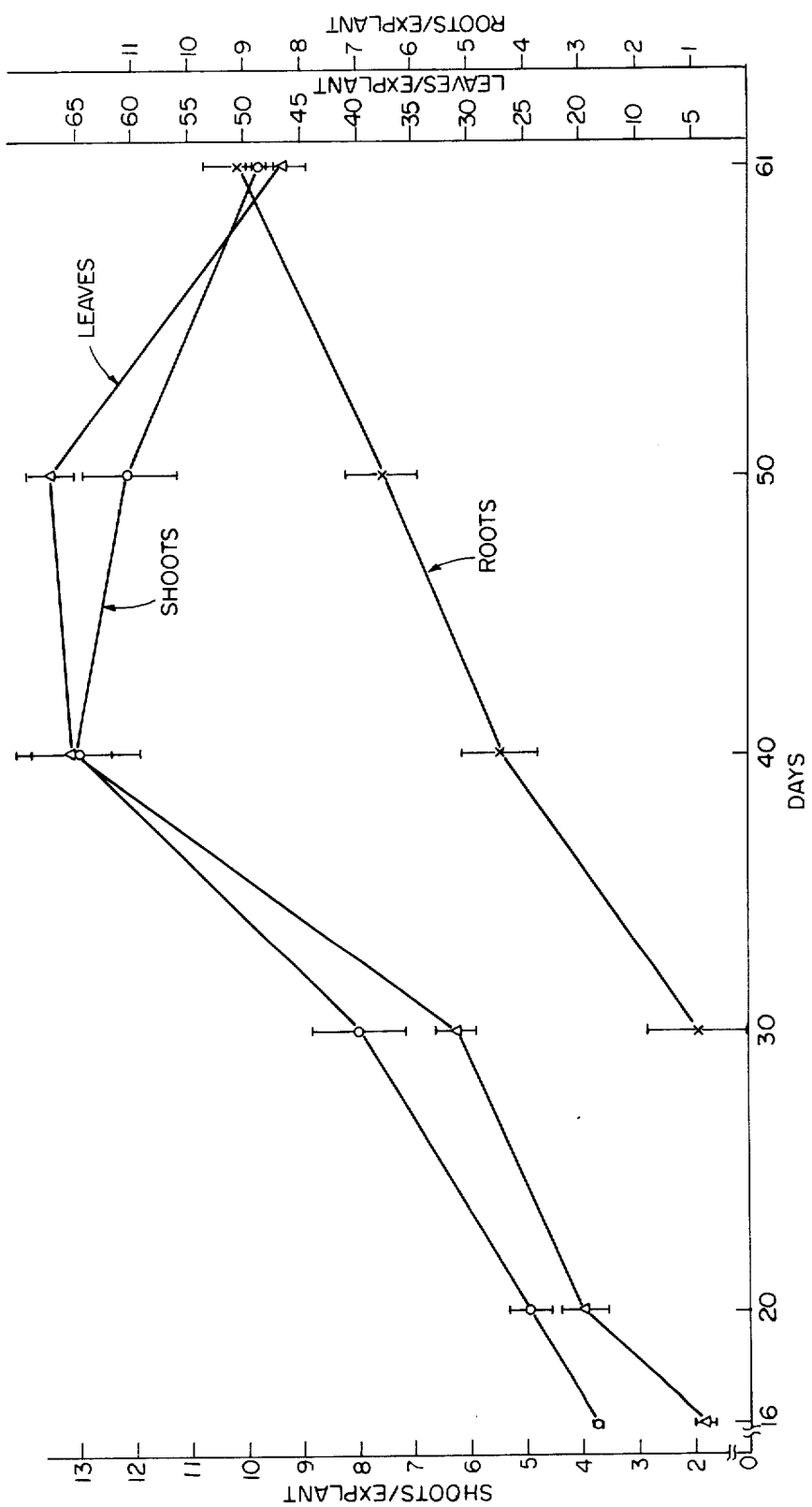

TISSUE CULTURE TECHNIQUE FOR ASEXUAL PLANT REPRODUCTION AND A MEDIUM FOR USE THEREWITH

FIELD OF THE INVENTION

This invention relates generally to a tissue culture method for the asexual propagation of plants and to a culture medium for use in the tissue culture process.

The propagation of plants through seeds has always suffered a number of limitations. The plants thus propagated may be quite variable, since they do not necessarily contain all the parental characteristics, and a significant proportion of a crop may consequently be of an unsalable quality. Additionally, proper germination of the seeds is dependent upon, and influenced by, such external conditions as weather, the nature and pH of the soil, organisms in the soil, the availability of water, temperature, light and a loss of vigor during storage of the seeds. The number of seed-propagated plants available for consumption is limited both by the seasonal availability of the crop, seed supply, and the amount of growing space.

Recent forecasts predicting an increasing food shortage in the world have stimulated efforts to discover more efficient and reliable methods for food production. In recent years, plant tissue culture methods have gained importance as a means for vegetative propagation of food, ornamental and medicinal crops owing to the ability of such a technique to produce rapid multiplication and proliferation of genetically uniform plants, thereby assuring that the desired characteristics of the selected donor plants are retained.

In the tissue culture technique, a piece of a donor plant is excised and placed in a culture medium comprising nutrients in the form of organic and inorganic compounds and hormones. Because the size of the excised plant part is generally in the order of two or three millimeters, the number of cultures which may be induced from a single donor plant may greatly exceed the number of seeds such a plant would ordinarily produce. The rate of multiplication thus attainable is even further enhanced by the fact that one need not wait for the plant to produce seeds but may excise plant parts at virtually any time during the plant's growth. Accordingly, the tissue culture technique enables timely increases of plant stock and hastens the availability of new varieties. Finally, the minimal size of the excised plant part lends itself to convenient storage under sterile conditions so that pest and plant disease problems conventionally associated with the maintenance of stock plants is virtually eliminated.

Conventionally, tissue culture techniques have been tailored to the stages of growth for the particular plant involved. These growth stages may be described as the induction stage, where the explant is established aseptically on the medium and allowed to respond to the medium via rapid growth and enlargement; the multiplication stage, wherein the explant produces a mass of undifferentiated cells called callus; the differentiation stage wherein the cells give rise to shoots and/or roots to form a plurality of separate plantlets; and the hardening stage wherein the plantlets are separated and allowed to develop from the heterotropic to the autotropic stage. During the induction stage, the explants have conventionally been placed in a nutritive medium containing organic and inorganic salts and growth regulators or growth hormones.

In an article entitled "Chemical Control of Adventitious Organ Formation in Lactuca Sativa Explants" by M. R. Doerschug, et al. (Amer. J. Bot. 54 (4): 410–413 (1967)), for example, kinetin (6-furfurylaminopurine) and adenine (6-aminopurine) are shown to promote the initiation of adventitious buds in excised cotyledons of Lactuca Sativa. A medium containing inorganic and organic salts, indoleacetic acid (IAA) and either kinetin or adenine were utilized to induce bud formation from cotyledon explants.

It is an object of the invention to promote a rapid proliferation of simultaneous shoot and root formation on a single culture medium.

It is another object of the invention to bring about rapid and multiple propagation of plants from the explant of a selected donor.

The culture technique and culture medium described herein are particularly suited for plants of the family Cruciferae. The technique basically comprises the steps of excising a part of the donor plant, culturing the excised part, hereinafter referred to as the explant, on a medium containing IAA, kinetin and a salt of adenine to induce differentiation of the explant into a plurality of plantlets, and transplanting the plantlets into soil.

The culture medium described herein promotes the simultaneous formation by the explant of shoots and roots so that rapid plant proliferation is achieved.

The disclosed technique and culture medium additionally lend themselves to a continuous or batch process whereby callus from the explant may be conveniently stored for a period in the order of a year or more and withdrawn as needed when required for propagation of a large quantity of plantlets so that plants may be timely grown therefrom as the need arises.

Further aspects and advantages of the invention will be apparent from the following description of the preferred embodiment.

BRIEF DESCRIPTION OF THE DRAWING

The sole FIGURE herein is a graphic representation of explant growth on the culture medium.

DESCRIPTION OF THE PREFERRED EMBODIMENT

The technique disclosed herein, as well as the culture medium used therewith, is particularly suited for plants of the family Cruciferae and basically comprises the steps of excising a part of the donor plant, culturing the excised part on a medium containing IAA, kinetin and a salt of adenine to induce differentiation of the explant into a plurality of plantlets, and the subsequent transplanting of the plantlets into the soil. As will be discussed in greater detail, the medium promotes the simultaneous formation of shoots and roots which form the plantlets and enables the plantlets to quickly transform to an autotropic state.

In accordance with one aspect of the invention, and as supported in the examples set forth below, an excised part of a donor plant is placed in a tissue culture medium hereinafter referred to as Medium A and containing the following nutrients of organic and inorganic salts and growth regulators:

| INORGANIC SALTS | (mg/l) |
|---|---|
| $KH_2PO_4$ | 300 |
| $KNO_3$ | 1000 |
| $NH_4NO_3$ | 1000 |
| $Ca(NO_3)_2 \cdot 4H_2O$ | 500 |

-continued

| | |
|---|---|
| $MgSO_4 \cdot 7H_2O$ | 71.6 |
| KCl | 65 |
| $MnSO_4 \cdot H_2O$ | 4.92 |
| $ZnSO_4 \cdot 7H_2O$ | 2.67 |
| $H_3BO_3$ | 1.6 |
| KI | 0.8 |
| NaEDTA | 37.2 |
| $FeSO_4 \cdot 7H_2O$ | 27.8 |
| ORGANIC SALTS | (mg/l) |
| Thiamine . HCl | 0.1 |
| Nicotinic Acid | 0.5 |
| Pyridoxine . HCl | 0.1 |
| My0-inositol | 100 |
| Glycine | 2 |
| Sucrose | 30,000 |
| Agar | 10,000 |
| GROWTH REGULATORS | (mg/l) |
| Indoleacetic Acid (IAA) | 1 |
| kinetin | 0.5 |
| adenine sulfate | 40 |

The above-described composition initiates the simultaneous formation by the excised tissue of shoots and roots to form a plurality of plantlets in the culture medium during a period of approximately 14 to 30 days.

In accordance with a second aspect of the invention, the excised part of the donor plant is first placed in another medium hereinafter referred to as Medium 1.

Medium 1 is utilized to induce and maintain callus formation on the excised plant part. The callus may be stored in this manner for a period in the order of a year or more until a need for duplicates of the donor plant arises, whereupon a portion of the callus is excised and placed on Medium A. Medium 1 contains the inorganic and organic salts, and the amounts therefor, indicated above. The growth regulators utilized is this medium, however, are:

1.86 mg./l of Naphthaleneacetic acid
2.25 mg/l $N_6$-Benzyladenine ($N_6BA$)

Further details and modifications to the preferred embodiment of the subject invention will become apparent hereinbelow wherein the utility of the present on various varieties of Cruciferae is demonstrated.

In ascertaining the preferred tissue culture method for asexually reproducing species of Cruciferae, a large of experiments were performed with lettuce of the 'Black Seeded Simpson' and 'Summer Bibb' varieties.

Lettuce seeds were sterilized for five minutes in a solution of Chlorox, (a trademark owned by the Chlorox Company for bleach) and rinsed several times with sterile distilled water. The seeds were then placed in sterilized petri dishes containing filter paper and distilled water and allowed to germinate in the dark for 4 to 5 days, After this period, the seedlings were dissected for various plant parts under aseptic conditions. These excised parts included the cotyledon, epicotyl, hypocotyl plumule and radicle. In general, the size of the explant varied from 1mm to 3mm.

Additionally, a head of lettuce of another variety obtained from a supermarket was used in these studies by excising 2-3mm pieces from the innermost leaves near the apical meristem.

All the plant parts thus obtained were planted onto the Medium 1 for callus induction and maintenance or onto Medium A for shoot root differentiation. The cultures on Medium 1 were maintained under dark conditions for up to six months and portions of the callus subsequently excised and transferred to Medium A. The cultures on Medium A were exposed to GroLux Lights for 30 days with a 16 hour daily light schedule at an intersity at $360\mu W/cm^2$. (GroLux is a trademark owned by GTE Sylvania for a lamp having a spectral output matched to the absorption spectrum, of Chlorophyll-A.)

In accordance with the invention, the same technique was utilized whether the culture contained callus or the actual plant part. A comparison of results obtained for the various plant parts as indicated in Table 1 below shows that optimum organogenesis was derived from the cotyledon and leaf.

TABLE I

Growth and Organogenesis of Various Seedling parts and entire plant parts on medium

| Plant Part | Rate of Organogenesis | Time to Organogenesis (Days) | No. of Shoots/Explant after 30 days | |
|---|---|---|---|---|
| | | | Var. 'Simpson.' | Var. 'Summer Bibb' |
| Cotyledon | 30/30 | 10 | 10 | 20 |
| Epicotyl | 30/30 | 15 | 6 | 11 |
| Hypocotyl | 27/30 | 20 | 8 | 13 |
| Plumule | 25/30 | 18 | 5 | 8 |
| Radicle | 20/30 | 30 | 5 | 5 |
| Leaf | 30/30 | 10 | 12 | 17 |

*indicates the number of differentiating explants/number of explants cultured.

Having thus determined that the cotyledon explants yielded optimum results, that part was utilized in the remaining tests.

The effect upon shoot, leaf, bud and root formation caused by variations in the concentration of the three growth regulators IAA, kinetin and adenine sulfate was investigated next by utilizing culture media with varying concentrations of each and examining the plantlets after a 30 day period. Tables 2a–b, 3a–b and 4a–b show the effects of singularly varying the concentration for culture of "Summer Bibb" and "Simpson" explants. Similarly, Tables 5a–c, 6a–c and 7a–c and 7a–c demonstrate the effects on "Summer Bibb" of varying two of the three regulator concentrations simultaneously. It may be observed from these tables that optimum results were obtained when the culture medium included 1 mg/l of IAA, 0.5 mg/l of kinetin and either 20 or 40 mg/l of adenine sulfate.

TABLE 2A (BLACK SEEDED SIMPSON)

| 0.5 mg/l Kinetin 40 mg/l Adenine Sulfate | EXPLANTS CULTIVATED | NO. WITH BUDS | NO. OF BUDS | NO. WITH SHOOTS | NO. OF SHOOTS | NO. WITH ROOTS | NO. OF ROOTS |
|---|---|---|---|---|---|---|---|
| +0.5 mg/l IAA | 20 | 20 | M | 20 | 8 | 13 | 5 |
| +1 mg/l IAA | 20 | 20 | H | 20 | 12 | 20 | 8 |

TABLE 2A-continued
(BLACK SEEDED SIMPSON)

| 0.5 mg/l Kinetin 40 mg/l Adenine Sulfate | EXPLANTS CULTIVATED | NO. WITH BUDS | NO. OF BUDS | NO. WITH SHOOTS | NO. OF SHOOTS | NO. WITH ROOTS | NO. OF ROOTS |
|---|---|---|---|---|---|---|---|
| +5 mg/l IAA | 20 | 20 | M | 16 | 5 | 12 | 6 |
| +10 mg/l IAA | 20 | 16 | M | 7 | 2 | 9 | 4 |
| +20 mg/l IAA | 20 | 13 | M | 2 | 1 | 8 | 4 |
| +50 mg/l IAA | 20 | 6 | S | 1 | 1 | 5 | 3 |
| +100 mg/l IAA | 20 | 2 | S | — | — | — | — |

S = 1-2 buds
M = 3-8 buds
H = more than 8 buds

TABLE 2B
(SUMMER BIBB)

| 0.5 mg/l Kinetin 40 mg/l Adenine Sulfate | PLANT PARTS CULTIVATED | NO. WITH BUDS | NO. OF BUDS | NO. WITH SHOOTS | NO. OF SHOOTS | NO. WITH ROOTS | NO. OF ROOTS |
|---|---|---|---|---|---|---|---|
| +0.5 mg/l IAA | 20 | 20 | M | 20 | 8 | 11 | 2 |
| +1 mg/l IAA | 20 | 20 | H | 20 | 20 | 14 | 4 |
| +5 mg/l IAA | 20 | 20 | M | 15 | 7 | 12 | 3 |
| +10 mg/l IAA | 20 | 16 | M | 8 | 2 | 12 | 2 |
| +20 mg/l IAA | 20 | 13 | M | 5 | 2 | 10 | 2 |
| +50 mg/l IAA | 20 | 6 | S | 1 | 1 | 5 | 1 |
| +100mg/l IAA | 20 | 2 | S | — | — | — | — |

S = 1-2 buds
M = 3-8 buds
H = more than 8 buds

TABLE 3A
BLACK SEEDED SIMPSON

| 1.0 mg/l IAA 40 mg/l Adenine Sulfate | NO. OF PLANT PARTS CULTURED | NO. WITH BUDS | NO. OF BUDS | NO. WITH SHOOTS | NO. OF SHOOTS | NO. WITH ROOTS | NO. OF ROOTS |
|---|---|---|---|---|---|---|---|
| +0.1 mg/l Kinetin | 20 | 17 | M | 16 | 7 | 16 | 7 |
| +0.5 mg/l Kinetin | 20 | 20 | H | 20 | 12 | 20 | 5 |
| +1 mg/l Kinetin | 20 | 20 | H | 20 | 9 | 18 | 2 |
| +5 mg/l Kinetin | 20 | 13 | M | 10 | 3 | — | — |
| +10 mg/l Kinetin | 20 | 7 | S | 2 | 1 | — | — |
| +50 mg/l Kinetin | 20 | 3 | S | — | — | — | — |

S = 1-2 buds
M = 3-8 buds
H = more than 8 buds

TABLE 3B
SUMMER BIBB

| 1.0 mg/l IAA 40 mg/l Adenine Sulfate | NO. OF PLANT PARTS CULTURED | NO. WITH BUDS | NO. OF BUDS | NO. WITH SHOOTS | NO. OF SHOOTS | NO. WITH ROOTS | NO. OF ROOTS |
|---|---|---|---|---|---|---|---|
| +0.1 mg/l Kinetin | 20 | 18 | M | 18 | 10 | 18 | 6 |
| +0.5 mg/l Kinetin | 20 | 20 | H | 20 | 20 | 20 | 4 |
| +1 mg/l Kinetin | 20 | 20 | H | 20 | 14 | 20 | 2 |
| +5 mg/l Kinetin | 20 | 15 | M | 11 | 2 | — | — |
| +10 mg/l Kinetin | 20 | 9 | S | 4 | 1 | — | — |
| +50 mg/l Kinetin | 20 | 4 | S | — | — | — | — |

S = 1-2 buds
M = 3-8 buds
H = more than 8 buds

TABLE 4A

ADENINE SULFATE VARIATION (BLACK SEEDED SIMPSON)

| 1.0 mg/l IAA 0.5 mg/l Kinetin | NO. OF PLANT PARTS CULTURED | NO. WITH BUDS | NO. OF BUDS | NO. WITH SHOOTS | NO. OF SHOOTS | NO. WITH ROOTS | NO. OF ROOTS |
|---|---|---|---|---|---|---|---|
| +5 mg/l adenine sulfate | 20 | 18 | M | 13 | 6 | 6 | 5 |
| +10 mg/l adenine sulfate | 20 | 19 | M | 15 | 7 | 10 | 8 |
| +20 mg/l adenine sulfate | 20 | 19 | H | 19 | 9 | 13 | 7 |
| +40 mg/l adenine sulfate | 20 | 20 | H | 20 | 12 | 17 | 6 |
| +80 mg/l adenine sulfate | 20 | 20 | H | 17 | 8 | 5 | 2 |
| +150 mg/l adenine sulfate | 20 | 12 | M | 6 | 3 | 3 | 1 |
| +200 mg/l adenine sulfate | 20 | 8 | M | 3 | 2 | 1 | 1 |

S = 1-2 buds
M = 3-8 buds
H = more than 8 buds

TABLE 4B

ADENINE SULFATE VARIATION (SUMMER BIBB)

| 1.0 mg/l IAA 0.5 mg/l KINETIN | NO. OF PLANT PARTS CULTURED | NO. WITH BUDS | NO. OF BUDS | NO. WITH SHOOTS | NO. OF SHOOTS | NO. WITH ROOTS | NO. OF ROOTS |
|---|---|---|---|---|---|---|---|
| +5 mg/l adenine sulfate | 20 | 18 | M | 17 | 6 | 6 | 2 |
| +10 mg/l adenine sulfate | 20 | 19 | M | 19 | 8 | 8 | 2 |
| +20 mg/l adenine sulfate | 20 | 19 | H | 19 | 15 | 10 | 3 |
| +mg/l adenine sulfate | 20 | 20 | H | 20 | 20 | 13 | 4 |
| +80 mg/l adenine sulfate | 20 | 20 | H | 18 | 14 | 7 | 2 |
| +150 mg/l adenine sulfate | 20 | 12 | M | 11 | 2 | 3 | 2 |
| +200 mg/l adenine sulfate | 20 | 8 | M | 7 | 1 | 1 | 1 |

S = 1-2 buds
M = 3-8 buds
H = more than 8 buds

TABLE 5A

'VARIETY SUMMER BIBB'
AVERAGE NUMBER OF SHOOTS FORMED PER EXPLANT
Concentration IAA = 0.1 mg/l

| ADENINE SULFATE (mg/l) | KINETIN (mg/l) | | | |
|---|---|---|---|---|
| | 0.1 | 0.5 | 5 | 10 |
| 5 | 2.6 | 4.0 | — | — |
| 10 | 3.0 | 4.8 | — | — |
| 20 | 3.4 | 7.6 | — | — |
| 40 | 3.2 | 7.2 | — | — |
| 80 | 2.0 | 3.8 | — | — |

TABLE 5B

'VARIETY SUMMER BIBB'
AVERAGE NUMBER OF LEAVES FORMED PER EXPLANT
IAA = 0.1 mg/l

| ADENINE SULFATE (mg/l) | KINETIN (mg/l) | | | |
|---|---|---|---|---|
| | 0.1 | 0.5 | 5 | 10 |
| 5 | 5.4 | 7.6 | — | — |
| 10 | 6.2 | 9.8 | — | — |
| 20 | 7.0 | 15.6 | — | — |
| 40 | 6.2 | 13.2 | — | — |
| 80 | 4.0 | 7.6 | — | — |

TABLE 5C

'VARIETY SUMMER BIBB'
AVERAGE NUMBER OF ROOTS FORMED PER EXPLANT
IAA = 0.1 mg/l

| ADENINE SULFATE (mg/l) | KINETIN (mg/l) | | | |
|---|---|---|---|---|
| | 0.1 | 0.5 | 5 | 10 |
| 5 | 1.2 | 0.8 | — | — |
| 10 | 1.3 | 1.0 | — | — |
| 20 | 1.8 | 1.2 | — | — |
| 40 | 1.3 | 1.2 | — | — |
| 80 | 1.2 | 0.6 | — | — |

TABLE 6A

'VARIETY SUMMER BIBB'
AVERAGE NUMBER OF SHOOTS FORMED PER EXPLANT
IAA = 1.0 mg/l

| ADENINE SULFATE (mg/l) | KINETIN (mg/l) | | | |
|---|---|---|---|---|
| | 0.1 | 0.5 | 5 | 10 |
| 5 | 3.6 | 7.0 | 2.2 | 2 |
| 10 | 4.8 | 7.8 | 1.8 | 1.6 |
| 20 | 8.2 | 12.8 | 1.4 | 1.0 |
| 40 | 11.6 | 20 | 0.6 | — |
| 80 | 6 | 7.2 | — | — |

TABLE 6B
'VARIETY SUMMER BIBB'
AVERAGE NUMBER OF LEAVES FORMED PER EXPLANT
IAA = 1.0 mg/l

| ADENINE SULFATE (mg/l) | KINETIN (mg/l) | | | |
|---|---|---|---|---|
| | 0.1 | 0.5 | 5 | 10 |
| 5 | 9.6 | 15.2 | 4.4 | 4.1 |
| 10 | 9.6 | 17.2 | 3.8 | 3.4 |
| 20 | 16.8 | 24.2 | 2.8 | 2.2 |
| 40 | 21.6 | 37.2 | 1.4 | — |
| 80 | 12.2 | 15.8 | — | — |

TABLE 6C
'VARIETY SUMMER BIBB'
AVERAGE NUMBER OF ROOTS FORMED PER EXPLANT
IAA = 1.0 mg/l

| ADENINE SULFATE (mg/l) | KINETIN (mg/l) | | | |
|---|---|---|---|---|
| | 0.1 | 0.5 | 5 | 10 |
| 5 | 2.8 | 1.4 | 0.6 | 0.4 |
| 10 | 3.0 | 1.8 | 0.4 | 0.1 |
| 20 | 3.2 | 2.0 | — | — |
| 40 | 4.4 | 2.4 | — | — |
| 80 | 2.2 | 1.4 | — | — |

TABLE 7A
'VARIETY SUMMER BIBB'
AVERAGE NUMBER OF SHOOTS FORMED PER EXPLANT
IAA = 10 mg/l

| ADENINE SULFATE (mg/l) | KINETIN (mg/l) | | | |
|---|---|---|---|---|
| | 0.1 | 0.5 | 5 | 10 |
| 5 | 1.4 | 1.8 | 2.2 | 1.2 |
| 10 | 1.2 | 2.2 | 1.8 | 0.8 |
| 20 | 1.0 | 1.2 | 1.4 | 0.6 |
| 40 | 0.8 | 0.8 | 1.2 | 0.6 |
| 80 | 0.2 | 0.4 | 0.4 | 0.2 |

TABLE 7B
AVERAGE NUMBER OF LEAVES FORMED PER EXPLANT
IAA = 10 mg/l
'VARIETY SUMMER BIBB'

| ADENINE SULFATE (mg/l) | KINETIN (mg/l) | | | |
|---|---|---|---|---|
| | 0.1 | 0.5 | 5 | 10 |
| 5 | 3 | 3.6 | 4.8 | 2.2 |
| 10 | 2 | 4.4 | 2.6 | 2.0 |
| 20 | 1.4 | 2.8 | 2.4 | 1.2 |
| 40 | 1.4 | 1.6 | 2.6 | 1.2 |
| 80 | 0.6 | 1.0 | 0.4 | 0.4 |

TABLE 7C
AVERAGE NUMBER OF ROOTS FORMED PER EXPLANT
IAA = 10 mg/l
'VARIETY SUMMER BIBB'

| ADENINE SULFATE (mg/l) | KINETIN (mg/l) | | | |
|---|---|---|---|---|
| | 0.1 | 0.5 | 5 | 10 |
| 5 | 1.4 | 1.0 | 0.8 | 0.4 |
| 10 | 1.4 | 0.8 | 0.8 | 0.4 |
| 20 | 1.2 | 0.8 | 0.6 | 0.2 |
| 40 | 0.6 | 0.4 | 0.4 | — |
| 80 | 0.4 | 0.4 | 0.2 | — |

The preferred age of the donor plant at the time of excision was determined by excising the cotyledon from donor plants having ages shown in Table 8 and culturing them in a medium comprising 1 mg/l IAA, 0.5 mg/l kinetin and 40 mg/l of adenine sulfate. As shown in Table 8, optimum shoot and root formation occurred for cotyledons excised from 4-day old donor plant.

TABLE 8
THE EFFECT OF LETTUCE COTYLEDON EXPLANT AGE ON ORGANOGENESIS
'VARIETY BLACK SEEDED SIMPSON'

| EXPLANT AGE (DAYS) | NO. OF SHOOTS | NO. OF LEAVES | NO. OF ROOTS |
|---|---|---|---|
| 2 | 8.89 | 34.13 | 0.91 |
| 4 | 9.14 | 36.00 | 1.86 |
| 8 | 7.66 | 33.73 | 0.53 |
| 11 | 5.37 | 13.59 | 0.66 |
| 16 | 3.88 | 8.44 | 0.29 |
| 22 | 2.66 | 8.04 | — |
| 25 | 2.82 | 6.62 | — |
| 28 | 2.53 | 3.14 | — |

The period for which the explants should be maintained on Medium A prior to transplanting was determined by placing cotyledon explants on the culture medium and subjecting them to $360\mu W/cm^2$ of broad spectral light for 16 hours per day. From the FIGURE, it may be seen that one may obtain maximum roots, shoot and leaf formation at approximately the 40th day and that the increase in shoot, root and leaf formation is at a maximum between the 30th and 40th days.

In addition to lettuce, radish, beet, may apple (*podophyllum peltatum*), and chrysanthemum have been successfully propagated utilizing the method and media describe above. Table VI below summarizes the results obtained with a medium comprising 1 mg/l of IAA, 0.5 mg/l kinetin and 40 mg/l adenine sulfate.

| PLANT | EXCISED PART | #SHOOTS/ EXPLANT | #ROOTS/ EXPLANT |
|---|---|---|---|
| Radish | cotyledon | 10–15 | 7–10 |
| Beet | cotyledon | 12–15 | 10–12 |
| May Apple | Rhizome | 4–5 | 6–8 |
| Chrysanthemum | Shoot tip with two pairs of leaf primordia | 8–10 | 4–6 |

I claim:

1. A method for asexually propagating plants comprising the steps of:
   a. excising a part of the donor plant;
   b. culturing the excised part on a nutrient medium containing to 1mg/l of IAA, 0.1 to 0.5 mg/l of kinetin, and 20-40 mg/l of a salt of adenine to promote the simultaneous growth of shoots and roots and induce the differentiation of the excised part into a plurality of plantlets; and
   c. transplanting the plantlets into soil.

2. The method of claim 1 wherein the simultaneous shoot and root formation is promoted by culturing the excised plant part on a medium containing approximately 1.0 mg/l of TAA, 0.5 mg/l of kinetin and 20 to 40 mg/l adenine sulfate.

3. The method of claim 2 wherein the donor plant is lettuce and the excised part is from the cotyledon.

4. The method of claim 2 wherein the donor plant is 3 to 5 days old.

5. The method of claim 1 wherein the culture is illuminated daily with broad spectrum light.

6. The method of claim 5 wherein the culture is subjected to a photoperiod of 16 hours of illumination and eight hours of darkness.

7. A method for asexually propagating plants comprising the steps of:
   a. excising a portion of a donor plant;
   b. culturing the excised portion in a first nutrient medium to promote callus formation;

c. culturing the callus onto a second nutrient medium containing -0.5 to 1 mg/l of IAA, 0.1 to 0.5 mg/l of kinetin, and 20 to 40 mg/l of a salt of adenine to promote the differentiation of the callus into shoots and roots which form a plurality of plantlets; and d. transplanting the plantlets into soil.

8. The method of claim 7 wherein the first medium contains naphthaleneacetic acid and $N_6$-Benzyladenine.

9. The method of claim 8 wherein the second medium contains -1.0 mg/l of IAA, 0.5 mg/l of kinetin, and 40 mg/l of adenine sulfate.

10. The method of claim 7 including the intermediate step of storing the formed callus to timely initiate the formation of plantlets as the need arises.

11. A tissue culture medium for use in the simultaneous formation of shoot and root by an excised plant part comprising suitable nutrients 0.5 to 1.0 mg/l of IAA, 0.1 to 0.5 mg/l of kinetin and 20 to 40 mg/l of adenine sulfate.

* * * * *